US006562348B2

(12) United States Patent
Hondalus et al.

(10) Patent No.: US 6,562,348 B2
(45) Date of Patent: May 13, 2003

(54) RECOMBINANT M. TUBERCULOSIS AUXOTROPHIC FOR LEUCINE AND VACCINES USING SAME

(75) Inventors: Mary K. Hondalus, Northborough, MA (US); Barry R. Bloom, Hastings on Hudson, NY (US); William R. Jacobs, Jr., City Island, NY (US)

(73) Assignee: Albert Einstein College of Medicine of Yeshiva University, Bronx, NY (US)

( * ) Notice: Subject to any disclaimer, the term of this patent is extended or adjusted under 35 U.S.C. 154(b) by 0 days.

(21) Appl. No.: 09/349,739

(22) Filed: Jul. 8, 1999

(65) Prior Publication Data

US 2002/0068067 A1 Jun. 6, 2002

(51) Int. Cl.[7] ........................ A61K 39/02; A61K 63/00; A61K 39/04; A61K 39/00; C12N 15/09

(52) U.S. Cl. .................. 424/200.1; 424/93.4; 424/93.2; 424/93.1; 424/234.1; 424/184.1; 424/235.1; 424/248.1; 435/69.3; 435/69.1

(58) Field of Search ........................... 424/200.1, 184.1, 424/234.1, 235.1, 248.1, 93.1, 93.2, 93.4; 435/91.4, 69.1, 172.1, 172.3, 252.3, 253.1, 69.3; 935/23, 65

(56) References Cited

U.S. PATENT DOCUMENTS

| | | | | |
|---|---|---|---|---|
| 5,972,700 A | * 10/1999 | Jacobs, Jr. et al. | ....... | 435/320.1 |
| 6,096,549 A | * 8/2000 | Pelicic et al. | ............... | 435/473 |
| 6,261,568 B1 | * 7/2001 | Gicquel et al. | .......... | 424/200.1 |
| 6,271,034 B1 | * 8/2001 | Bardarov et al. | ........... | 435/472 |

FOREIGN PATENT DOCUMENTS

WO WO 9532277 * 11/1995

OTHER PUBLICATIONS

Bange et al. In: Abstracts of the 96th General Meeting of the American Society for Microbiology, New Orleans, Louisiana, May 19–23, pp. 131, abstract U–173, 1996.*

Collins et al. In: Abstracts of the General Meeting of the American Society for Microbiology, Atlanta, Georgia, May 17–21, vol. 98, pp. 241, abstract E–43, 1998.*

Collins et al. In: Abstracts of the 96th General Meeting of the American Society for Microbiology, New Orleans, Louisiana, May 19–23, pp. 131, abstract U–134, 1996.*

Oh et al. J. Biol. Chem. 274: 15712–15718, May, abstract, 1999.*

Cleston et al. Biochem. Biophys. Res. Commun. 219 (1): 146–149, abstract, 1996.*

Balasubramanian et al. J. Bacteriol. 178: 273–279, Jan. 1996.*

Aldovini et al, The uraA locus and homologous recombination in mycobacterium bovis BCG. J. Bacteriol., 175:7282–89, 1993.

Azad et al., Gene Knockout reveals a novel gene cluster for the synthesis of a class of cell wall lipids unique to pathogenic mycobacteria. J. Biol. Chem., 272:16741–45, 1997.

Azad et al., Targeted replacement of the mycocerosic and synthase gene in mycobacterium bovis BCG produces a mutant that lacks mycosides. Proc. natl. Acad. Sci, USA, 93:4787–92, 1996.

Bange et al., Leucine auxotrophy restricts growth of Mycobacterium bovis BCG in macrophages. Infect. Immun., 64:1794–99, 1996.

China Tuberculosis Control Collaboration, Results of directly observed short–course chemotherapy in 112 842 Chinese patients with smear–positive tuberculosis. Lancet, 347:358–62, 1996.

Cole et al., Deciphering the biology of mycobacterium tuberculosis from the complete genome sequence. Nature, 393:537–44, 1998.

Desai et al., A nutrient–permeable channel on the intraerythrocytic malaria parasite. Nature, 362:643–646, 1993.

Dubos and Schaefer, Antituberculous immunity induced in mice by virulent primary infection. Am. Rev. Tubercolosis Pulmonary Dis., 74:541–51, 1956.

Gulieria et al., Auxotrophic vaccines for tuberculosis. Nature Med., 2:334–37, 1996.

Horwitz and Silverstein, Legionnaires' disease bacterium (Legionella pneumophilia) multiples intracellularly in human monocytes. J. Clin. Invest. 66:441–50, 1980.

Husson et al., Gene replacement and expression of foreign DNA in mycobacteria. J. Bacteriol., 172:519–24, 1990.

Kalpana et al., Insertional mutagenesis and illegitimate recombination in mycobacteria. Proc. Natl. Acad. Sci. USA, 88:5433–37, 1991.

Lange et al., Verification of the role of PCP 4–monooxygenase in chlorine elimination from pentachlorophenol by flavobacterium sp. strain ATCC 39723. Biochem. Biophys. Res. Commn. 219:146–49, 1996.

Marquis et al., Intracytoplasmic growth and virulence of Listeria monocytogenes auxotrophic mutants. Infect. Immun., 61:3756–60, 1993.

(List continued on next page.)

*Primary Examiner*—S. Devi
(74) *Attorney, Agent, or Firm*—Amster, Rothstein & Ebenstein

(57) ABSTRACT

The present invention provides a recombinant *M. tuberculosis* mycobacterium that is auxotrophic for leucine. The present invention also provides a vaccine comprising a recombinant *M. tuberculosis* mycobacterium that is auxotrophic for leucine, as well as a method for treating or preventing tuberculosis in a subject comprising administering to the subject a recombinant *M. tuberculosis* mycobacterium that is auxotrophic for leucine in an amount effective to treat or prevent tuberculosis in the subject.

16 Claims, 11 Drawing Sheets

OTHER PUBLICATIONS

Mcadam et al., In vivo growth characteristics of leucine and methionine auxotrophic mutants of Mycobacterium bovis BCG generated by transposon mutagenesis. Infect. Immun., 63:1004–12, 1995.

McFadden, Recombination in mycobacteria. Mol. Microbiol. 21:205–11, 1996.

Murray and Lopez, Alternative projections of mortality and disability by cause 1990–2020: Global Burden of Disease Study. Lancet, 349:1498–1504, 1997.

Murray and Salomon, Modeling the impact of global tuberculosis control strategies. Proc. Natl. Acad. Sci. USA, 95:13881–86, 1998.

Pelicic et al., Efficient allelic exchange and transposon mutagenesis in mycobacterium tuberculosis. Proc. Natl. Acad. Sci. USA, 94:10955–60, 1997.

Reyrat et al., The urease locus of mycobacterium tuberculosis and its utilization for the demonstration of allelic exchange in mycobacterium bovis bacillus Calmette–Guerin. Proc. Natl. Acad. Sci. USA, 92:8768–72, 1995.

Sander et al., Rpsl+: a dominant selectable marker for gene replacement in mycobacteria. Mol. Microbiol., 16:991–1000, 1995.

Schwab, et al., A putative pore in the parasitophorous vacuole membrane of Toxoplasma gondii identified by mcroinjection of fluorescent probes. Mol. Biol. Cell 3(Suppl):303a, Abstract 1757, 1992.

Stover et al., New use of BCG for recombinant vaccines. Nature, 351:456–60, 1991.

* cited by examiner

Southern Analysis of *leuD* mutant

Inactivation of *leuD* confers leucine auxotrophy in *M. tuberculosis*

*In vitro* growth of
H37Rv WT, *leuD*⁻ mutant, and complemented strains

Growth of H37Rv wildtype, LeuD- mutant and complemented strain in murine bone marrow derived macrophages Survival of Mice vaccinated with either *M. tuberculosis leuD-* or BCG

SEQUENCE LISTING

```
<160> NUMBER OF SEQ ID NOS:  4

<210> SEQ ID NO 1
<211> LENGTH: 20
<212> TYPE: DNA
<213> ORGANISM: Artificial Sequence
<220> FEATURE:
<221> NAME/KEY: primer
<222> LOCATION:
<223> OTHER INFORMATION: primer Pleu 1
```

-continued

<400> SEQUENCE: 1
tgaacaccgc ctttggcaat 20

<210> SEQ ID NO 2
<211> LENGTH: 20
<212> TYPE: DNA
<213> ORGANISM: Artificial Sequence
<220> FEATURE:
<221> NAME/KEY: primer
<222> LOCATION:
<223> OTHER INFORMATION: primer Pleu 2

<400> SEQUENCE: 2
gccttacgca ccgatgcctt 20

<210> SEQ ID NO 3
<211> LENGTH: 20
<212> TYPE: DNA
<213> ORGANISM: Artificial Sequence
<220> FEATURE:
<221> NAME/KEY: primer
<222> LOCATION:
<223> OTHER INFORMATION: blunt forward HindIII primer

<400> SEQUENCE: 3
aagcctttca cacccactct 20

<210> SEQ ID NO 4
<211> LENGTH: 27
<212> TYPE: DNA
<213> ORGANISM: Artificial Sequence
<220> FEATURE:
<221> NAME/KEY: primer
<222> LOCATION:
<223> OTHER INFORMATION: blunt reverse HindIII primer

<400> SEQUENCE: 4
gacaagcttt cgcccggttc tacgcct 27

RECOMBINANT M. TUBERCULOSIS AUXOTROPHIC FOR LEUCINE AND VACCINES USING SAME

STATEMENT OF GOVERNMENT INTEREST

This invention was made with government support under NIH Grant Nos. AI-45244 and AI-26170. As such, the United States government has certain rights in this invention.

BACKGROUND OF THE INVENTION

Approximately one third of the world's population is infected with *Mycobacterium tuberculosis* (MTB), the causative agent of human tuberculosis (TB). MTB is responsible for 2–3 million deaths annually, giving it the dubious distinction of being the leading cause of death due to a single infectious agent. In addition, TB ranks seventh in causes of global mortality and disability, and if current predictions prove correct, it will remain among the top 10 causes of disease, well into the next century (Murray and Lopez, *Lancet,* 349:1498-1504 (1997)). Directly observed treatment, short-course (DOTS) is the tactic proposed by the World Health Organization (WHO) to control the global TB crisis (Murray and Solomon, *PNAS USA,* 95:13881–13886 (1998)). DOTS has proven to be an effective strategy in several national TB control programs, with cure rates approaching 90% (*Lancet,* 347:358-362 (1996)). However, since global implementation of DOTS programs is occurring at a slow-moving pace, it is likely that additional measures will be needed to stem the tide of TB mortality. It has been estimated that the introduction of a new vaccine of only 50% efficacy could decrease the incidence of TB by 36 million cases, saving 9 million lives (Murray and Salomon, 1998). Thus, by coupling efficacious vaccination with effective treatment, greater success in global TB management would be anticipated.

Bacille Calmette-Guerin (BCG), an attenuated strain of *M. bovis,* is the currently available vaccine for the prevention of tuberculosis. It was created empirically by repeated passage in the laboratory, and for reasons that are as yet undefined, it is avirulent in immunocompetent hosts. In several animal models of infection, BCG has been demonstrated to induce protective immunity against MTB. Since its implementation in 1928 as a TB vaccine, more doses of BCG have been administered than any other vaccine, as an estimated 3 billion people have received BCG vaccination for the prevention of tuberculosis. Although the use of BCG is unquestionably safe in immunocompetent individuals, it has shown itself to be of variable efficacy. While in certain populations, vaccination with BCG has been highly effective in preventing tuberculosis, in others it has failed miserably. In the largest clinical trial that took place in India involving more that 100,000 persons, BCG exhibited a calculated protective efficacy of zero. Thus, the generation of an improved vaccine(s) to replace BCG and to prevent tuberculosis is urgently needed.

Relative to wildtype *M. tuberculosis,* 15–16 regions of the MTB genome are not represented in BCG. Eleven of these segments cannot be found even in virulent strains of *M. bovis;* of the remaining 5, 4 are missing from all BCG strains examined. It is probable that one or more of the 38 open reading frames (ORFs) specifically missing from BCG are required for virulence. Of interest, is the finding that a number of predicted transcriptional regulators identified by the H37Rv genome sequencing project (Cole, et al., *Nature,* 393:537–544 (1998)) would be located in these BCG deletions. The loss of a regulatory protein would be expected to affect multiple genetic loci and could lead to deranged gene expression in vivo. Consistent with this hypothesis, is the demonstration that reintroduction of one of these deleted regions into BCG results in the repression of at least 10 proteins and the upregulated expression of others. It is conceivable that potentially immunogenic and immunoprotective antigens might be missing from or inappropriately expressed in BCG, and therefore, compromising the immune response generated from this vaccine. For example, it has been noted that the gene for ESAT 6, a highly immunogenic, secreted protein of *M. tuberculosis,* is located within one of these deleted chromosomal regions. It has been demonstrated that protective immunity against experimental tuberculosis can be provided by prior immunization with supernatants containing a mixture of MTB secreted antigens, of which ESAT 6 is one. It is possible, that if one or more of the proteins encoded within the deleted regions were present at vaccination, the immune response elicited might be more efficacious.

It also has been demonstrated in both mice and guinea pigs that primary infection with MTB will induce resistance to re-infection (Dubos and Schaefer, *Ann. Rev. Tuberculous Pulmonary Dis.,* 74:541–551 (1956); Kanai and Yanagisawa, *Jap. J. Med. Sci. and Biol.,* 8:115–127 (1955)). Thus, it is feasible that a vaccine could be created by the rational deletion of genes of MTB, promoting the attenuation of, but preserving the immunogenicity and protectiveness of the bacillus. Ideally, such a vaccine would provide better protection than BCG.

An approach to the creation of vaccine strains that are avirulent yet immunogenic that has proved to be successful in other systems is the introduction of mutations conferring auxotrophy, or specific requirements for growth. For example, aromatic amino acid auxotrophs of *Salmonella typhimurium, Shigella flexneri, Bordetella pertussis,* Yersinia spp., *Pasteurella multocida, Bacillus anthrasis* and *Corynebacterium pseudotuberculosis* (Simmons, et al., *Infect. Immun.,* 65:3048–3056 (1997)) have displayed reduced virulence while exhibiting protection in various in vivo experimental systems. Similarly, purine and pyrimidine auxotrophs of Salmonella spp are attenuated in vivo. In addition, Bacon and colleagues created a strain of *S. typhimurium* that required exogenous leucine for growth and showed that the strain had diminished virulence for mice (Bacon, et al., *Brit. J. Exp. Path.,* 31:714–723 (1950)). Likewise, a leucine auxotroph of BCG, created by insertional disruption of leuD, a gene essential for leucine biosynthesis, failed to grow in either immunocompetent (McAdam, et al., *J. Clin. Invest.,* 66:441–450 (1995)) or immunodeficient SCID mice (Guliera, et al., *Nature Med.,* 2:334–337 (1996)).

SUMMARY OF THE INVENTION

The present invention provides a recombinant *M. tuberculosis* mycobacterium that is auxotrophic for leucine. The present invention also provides a vaccine comprising a recombinant *M. tuberculosis* mycobacterium that is auxotrophic for leucine, as well as a method for treating or preventing tuberculosis in a subject comprising administering to the subject a recombinant *M. tuberculosis* mycobacterium that is auxotrophic for leucine in an amount effective to treat or prevent tuberculosis in the subject. Additional objects of the present invention will be apparent from the description which follows.

DETAILED DESCRIPTION OF THE INVENTION

Figure 1:
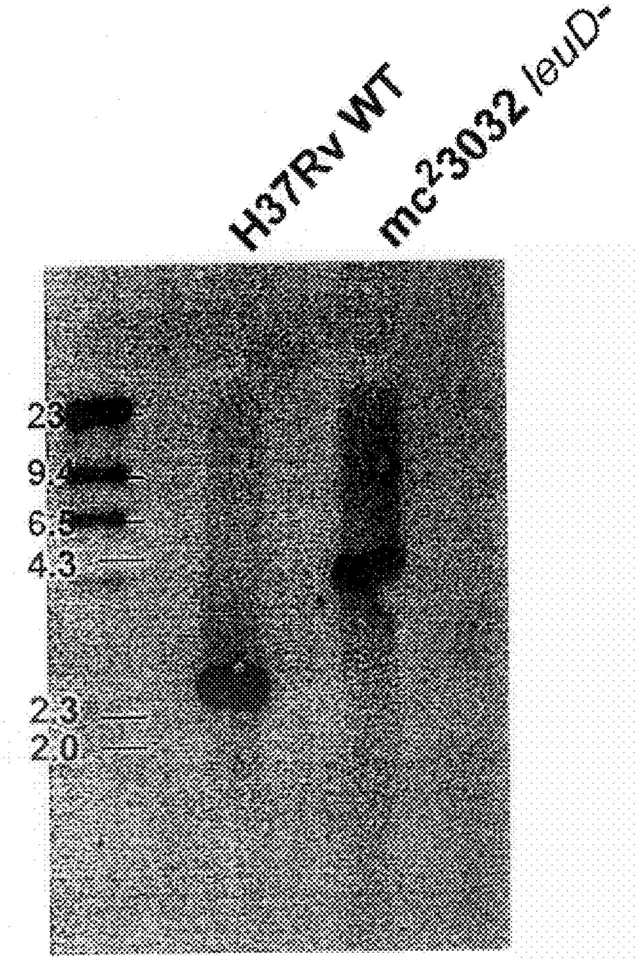
FIG. 1. Southern blot analysis of wildtype H37Rv and leuD− $mc^2$3032. Genomic DNA from wildtype H37Rv (lane 1) and the leucine auxotroph $mc^2$3032 (lane 2) was isolated, digested with Acc65I, and probed with the 600 bp leuD gene. Molecular weight markers (kb) are indicated on the left.

The present invention provides a recombinant *M. tuberculosis* mycobacterium that is auxotrophic for leucine. Preferably, the mycobacterium contains a mutation such as a deletion or point mutation of the leuD gene. Such a mutation may be generated in *M. tuberculosis* using the methods described in further detail below. In addition, it is also within the confines of the present invention that the recombinant *M. tuberculosis* auxotrophic for leucine may be generated using the methods described in copending U.S. application Ser. No. 09/350,048, U.S. Pat. No. 6,271,034 entitled “One Step Allelic Exchange in Mycobacteria Using In Vitro Generated Conditional Transducing Phages,” filed Jul. 8, 1999, and copending U.S. application Ser. No. 09/350,047, U.S. Pat. No. 6,423,545 entitled “Unmarked Deletion Mutants of Mycobacteria and Methods of Using Same,” filed Jul. 8, 1999, the contents of which are hereby incorporated by reference in their entirety.

The present invention also provides a vaccine comprising a recombinant *M. tuberculosis* mycobacterium that is auxotrophic for leucine, and a method for treating or preventing tuberculosis in a subject in need of such treatment or prevention using the vaccine. In this regard, the vaccine containing the recombinant mycobacteria of the present invention may be administered in conjunction with a suitable pharmaceutical carrier. Mineral oil, alum, synthetic polymers, are representative examples of suitable carriers. Vehicles for vaccines and therapeutic agents are well known in the art and the selection of a suitable vehicle is well within the skill of one skilled in the art. The selection of a suitable vehicle is also dependent upon the manner in which the vaccine or therapeutic agent is to be administered. The vaccine or therapeutic agent may be in the form of an injectable dose and may be administered intramuscularly, intravenously, orally, intradermally, or by subcutaneous administration. It also within the confines of the present invention that the vaccine may be formulated with a carrier to render the vaccine more immunogenic. Such immunogenicity enhancing agents are well known in the art.

The present invention is described in the following Experimental Details Section which is set forth to aid in the understanding of the invention, and should not be construed to limit in any way the invention as defined in the claims which follow thereafter.

Experimental Details Section

A. Materials and Methods

Bacterial Strains and Culture Methods

Liquid cultures of *M. tuberculosis* H37Rv (H37Rv), and *M. bovis* BCG strain Pasteur (BCG-P), $mc^2$3024 and $mc^2$3035 were grown in Middlebrook 7H9 broth (Difco BRL) supplemented with 0.2% glycerol, 0.05% Tween 80, and 10% Middlebrook OADC (Difco) and constituted minimal media. Solid cultures were grown on 7H10 agar supplemented as above, and in addition, 100 ug/ml of cyclohexamide was added to thwart fungal contamination. Strain $mc^2$3032 (H37Rv $leuD^-$) was cultured on minimal media supplemented with 50 ug/ml 1-leucine (Sigma Chemical Co., St. Louis, Mo.) referred to as complete media. When necessary, hygromycin B (Boehringer Mannheim, Indianapolis, Ind.) and kanamycin (Sigma) were added at final concentrations of 50 ug/ml and 20 ug/ml respectively. Bacterial growth was monitored by measuring optical density of the broth cultures over time. In so doing, log phase cultures were diluted to optical density 600 nm ($O.D._{600nm}$) of 0.05 and then every 24 h 0.5 ml of culture was removed, diluted with 0.5 ml of 10% formalin, and the $O.D._{600nm}$determined. All cultures were grown at 37° C.

Plasmid Construction, Allelic Replacement, and Construction of Complementing Strains To isolate the leuCD operon primers Pleu1 (5'-TGAACACCGCCTTTGGCAAT-3')(SEQ ID NO:1) and Pleu2 (5'-GCCTTACGCACCGATGCCTT-3')(SEQ ID NO:2) were designed using the *M. tuberculosis* genome sequence data base (Cole, et al., *Nature,* 393:537–544 (1998)) to amplify 3342 bp DNA fragment from *M. bovis* BCG (strain Pasteur) chromosomal DNA containing the leuC and leuD genes symmetrically flanked by about 0.6 kb homologous DNA sequence each side. This PCR product was cloned into the unique EcoRV site of pBluescript $II^+KS$ plasmid by blunt end ligation to generate pYUB595. A deletion of 359 bp in the leuD gene was generated by cleavage with SphI and SauI and marked with the res-hyg-res gene cassette introduced by blunt end ligation. The resulting plasmid, pYUB599, was digested with XbaI and HindIII to produce a 3342 bp DNA fragment containing leuCD6::res-hyg-res which was ligated to NotI digested pMP7 by blunt-end ligation generating pMH10.1. pMP7 is a Mycobacteria-*E.coli* shuttle vector containing an aph gene conferring kanamycin resistance and which is functional in both bacterial species, along with the counterselectable marker sacB from *B. subtilis* which confers lethality in the presence of sucrose. H37Rv was grown to an $O.D._{600nm}$ of 0.8, washed twice at RT in 10% glycerol, and resuspended in the same at ½0th of the initial culture volume. Four hundred $\mu$l of cells in a 0.2 cm cuvette were transformed with approximately 1 $\mu$g of pMH10.1 using a Gene Pulser (Bio-Rad) set at 2.5 kV, 25 UF, and 1000 ohms. Immediately following electroporation, the cells were transfered to tubes containing 1 ml of complete 7H9 media and incubated overnight at 37° C. The following day, the cells were plated on leucine supplemented 7H10 agar with 50 $\mu$g/ml of hygromycin. Hygromycin resistant ($hgm^r$) colonies appeared approximately 4 weeks later and were determined to be both sucrose sensitive (growth on 3% sucrose agar was lethal) ($suc^s$) and kanamycin resistant. Ten cultures of 10 individual $hgm^r/suc^s$ clones were established and grown for a week in media with 50 $\mu$g/ml hygromycin and 50 $\mu$g/ml of leucine. Aliquots of serial 10-fold dilutions of each individual culture were plated onto 7H10 agar supplemented with hygromycin, leucine and 3% sucrose. 334 $hgm^r/suc^r$ clones arising from the original 10 $hgm^r$ transformants were picked into the wells of 96-well plates which contained complete 7H9 media supplemented with leucine. Following 5 days of expansion at 37° C., the cultures were replica plated onto minimal media (no leucine) and rich media (leucine) with hygromycin or kanamycin. Eleven clones were found to be $hgm^r/kan^s/leu^-$. Southern blotting of these clones confirmed that these clones had undergone an allelic replacement event (FIG. 1). To create the leuD complementing strains $mc^23034$ and $mc^23035$, a leuD containing fragment was amplified by PCR from pYUB508, a plasmid carrying leuD, a using the blunt forward 5'AAGCCTTTCACACCCACTCT3' (SEQ ID NO 3)and Hind III reverse primer a 5'GACAAGCTTTCGCCCGGTTCTACGCCT3' (SEQ ID NO: 4). The resultant 600 bp PCR fragment was digested with HindIII and ligated to both pMV261 and pMV306 previously digested with MscI/HindIII; placing leuD in-frame and under the contol of the mycobacterial hsp60 heat shock promoter. pMV261 and pMV306 are mycobacterial-*E. coli* shuttle vectors, containing an ori E and aph gene and they are either extrachomosomal (pMV261) or integrative (pMV306) in mycobacteria spp. Strain $mc^23032$ was then transformed with the episomal and integrative complementing plasmids, using conditions described above. The transformants obtained did not require exogenous leucine for growth. Strain $mc^23034$ is complemented in multicopy and $mc^23035$ is complemented in single copy.

Southern Blotting

Genomic DNA was isolated from growing cultures of *M. tuberculosis* as follows: Bacteria from a 15 ml culture was pelleted and all media removed. Two ml of a 3:1 chloroform:methanol solultion was added and the pellet vortexed (approximately 1 min) until the bacteria were lysed, as evidenced by a clearing of the bottom layer. Two ml of Tris buffered phenol (pH8) was added and the solution was vortexed. Then 3 ml of guanidinium thiocyanate buffer (4M guanidinium thiocyanate; 0.1M Tris pH 7.5; 1% β-mercaptoethanol; 0.5% sarkosyl) was added, the mixture vortexed and solution was centrifuged at 500×g for 15 min. Following centrifugation, the aqueous layer was removed, and the DNA was precipitated by addition of an equal volume of isopropanol. Approximately 1 ug of DNA per strain was digested with Asc65I and then separated on a 0.7% agarose gel. Chemiluminescent Southern blotting was done using the ECL direct nucleic acid labeling and detection system (Amersham) and was performed according to manufacturer's recommendations. A 600 bp PCR fragment of leuD (described above) was used as a probe.

Reversion or Suppressor Mutant Analysis

A 100 ml culture of *M. tuberculosis* strain $mc^23032$ was grown to an $O.D._{600nm}$ of 1.0–2.0 in leucine supplemented medium without hygromycin. The titer of the culture was determined retrospectively by dilution plating on agar plates supplemented with leucine. For analysis of reversion frequency, the entire culture was pelleted and resuspended in 2 ml of leucine-free medium. The 2 ml re-suspension was spread over 20 plates of minimal (leucine-free) 7H10 agar supplemented with OADC and glycerol, as described.

Macrophages

Primary murine bone marrow-derived macrophages (BMM) were obtained by flushing the femurs of BALB/cJ with 5 ml of cold cation-free phosphate buffered saline (Gibco, Grand Island, N.Y.). The marrow was dispersed by gentle pipetting, pelleted by centrifugation, and the cells were resuspended in Dulbecco's Modified Eagle's Media (DMEM) (Gibco) supplemented with 20% L-929 cell conditioned medium, 10% heat-inactivated fetal calf serum (FCS), 2 mM glutamine, 100 U/ml penicillin G and 100 ug/ml streptomycin. The cells were cultured on non-tissue culture treated, 150-mm plastic petri dishes, at 37° C., 5% $CO_2$ for 5–7 days at which time monolayers of macrophages were readily apparent. For use in assays, cells were removed from the petri dishes using 5 mM EDTA in cation-free PBS, pelleted, and then resuspended in antibiotic free media supplemented with 10% FCS, and 5% L-929 cell conditioned media. Approximately $2\times10^5$ cells were distributed per wells of tissue culture-treated 8-well chamber slides (Nalge Nunc International, Naperville, Ill.).

Mouse Strains and in Vivo Infection

Female BALB/cJ mice were obtained from Jackson Laboratories (Bar Harbor, Me.) and immunized at approximately 8 weeks of age. BALB/c SCID mice were bred in the Animal Facility of Albert Einstein College of Medicine (Bronx, N.Y.). Both male and female SCID mice were used and were infected between 8–12 weeks of age. In preparation for immunization or infection of mice, titered frozen aliquots of the bacterial strains were thawed, diluted in phosphate buffered saline (PBS) with 0.05% Tween 80™ (PBS-tween), and sonicated (10 seconds) to disperse clumps of bacteria. Even though the frozen bacterial aliquots had been titered previously, the titer of the inoculum was reconfirmed at the time of injection by dilution plating of the injection stock. Groups of mice were injected intravenously in the tail veins with H37Rv, BCG-P, $mc^23032$, $mc^23034$ or $mc^23035$ in 100 $\mu$l PBS-tween. In order to monitor bacterial clearance or growth, at various times post-injection, 4–5 mice from each experimental group were sacrificed and their spleens, livers, and lungs were aseptically removed. Each spleen and lung were placed in plastic bags containing 4.5 ml of PBS-tween with 100 $\mu$g/ml carbenicillin; each liver placed in bags with 9.5 ml of the same. The tissue was disrupted by placement of the bag containing the organ in a Stomacher-80 (Seward). Serial 10-fold dilutions of the tissue homogenate were plated onto 7H10 agar containing 0.2% glycerol, 10% OADC, 100 $\mu$g/ml cyclohexamide, and supplemented with leucine, and/or antibiotic when appropriate. Plates were incubated at 37° C. Colony forming units (CFU) were determined 3–4 wk later.

In SCID mouse infection experiments, groups of mice were challenged with approximately $1\times10^4$ CFU of H37Rv, $1\times10^4$ CFU of $mc^23034$, $1\times10^4$ CFU of $mc^23305$, or $1\times10^6$ CFU of $mc^23032$. To document the challenge dose, animals were sacrificed at 18 hr, organs removed, and CFU determined, as described above. Thirteen mice per experimental group were then followed for survival studies. At the time of death, organs were removed from animals that succumbed to infection and CFU determined, as described previously. SCID mice challenged with $mc^22032$ remained healthy, and were sacrificed 22 weeks post-infection and organ burdens likewise assessed.

In immunization studies, BALB/cJ mice were immunized with $5\times10^6$ CFU of either BCG-P or $mc^22032$. At 9 weeks post-immunization, both vaccinated and unvaccinated control mice were intravenously challenged with $1\times10^6$ *M. tuberculosis* strain Erdman. Bacterial organ burdens over time post-challenge were determined, as described above, and 15 mice per experimental group were monitored for survival.

B. Results

Creation of the leuD Mutant of *M. tuberculosis*

Figures 2A, 2B:
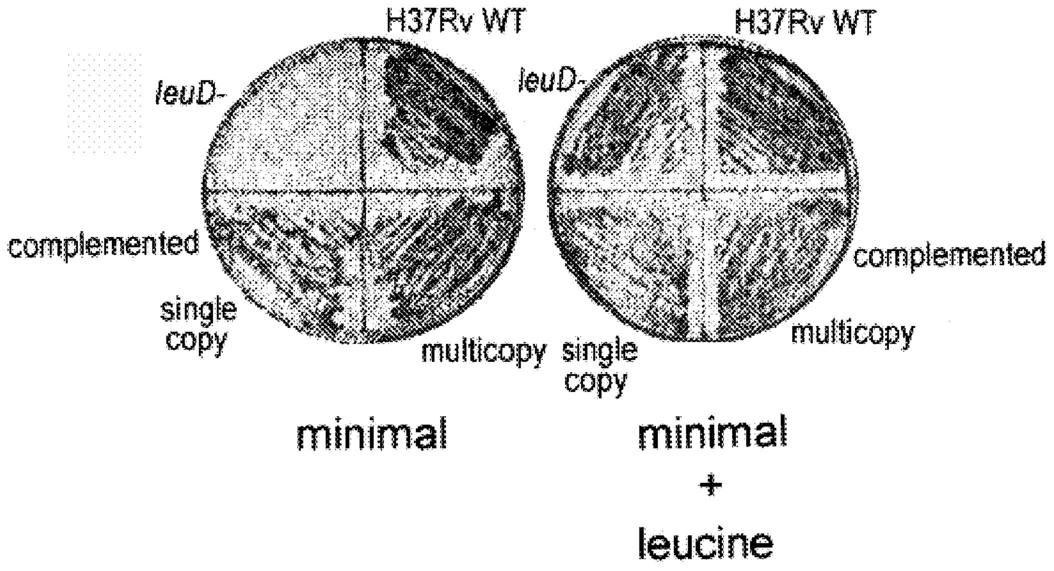
FIGS. 2A–2C. Inactivation of leuD confers leucine auxotrophy. A) Growth of strains of *M. tuberculosis* on minimal media without leucine or minimal media supplemented with 50 $\mu$g/ml of leucine and B) growth in Middlebrook 7H9 broth with (closed symbols and solid lines) and without (open symbols and broken lines) supplementation of 50 $\mu$g per ml of leucine. Circles: H37Rv wildtype; squares: $mc^2$3032 $LeuD^-$; triangle:$mc^2$3034 (multicopy complemented strain); diamond:$mc^2$3035 (single copy complemented strain). The various strains were cultured in 7H9 media supplemented with leucine, then pelleted, washed, and resuspended or streaked onto media with and without leucine supplementation. The optical density ($O.D._{600}$) of broth cultures were determined daily.
Figure 2C:
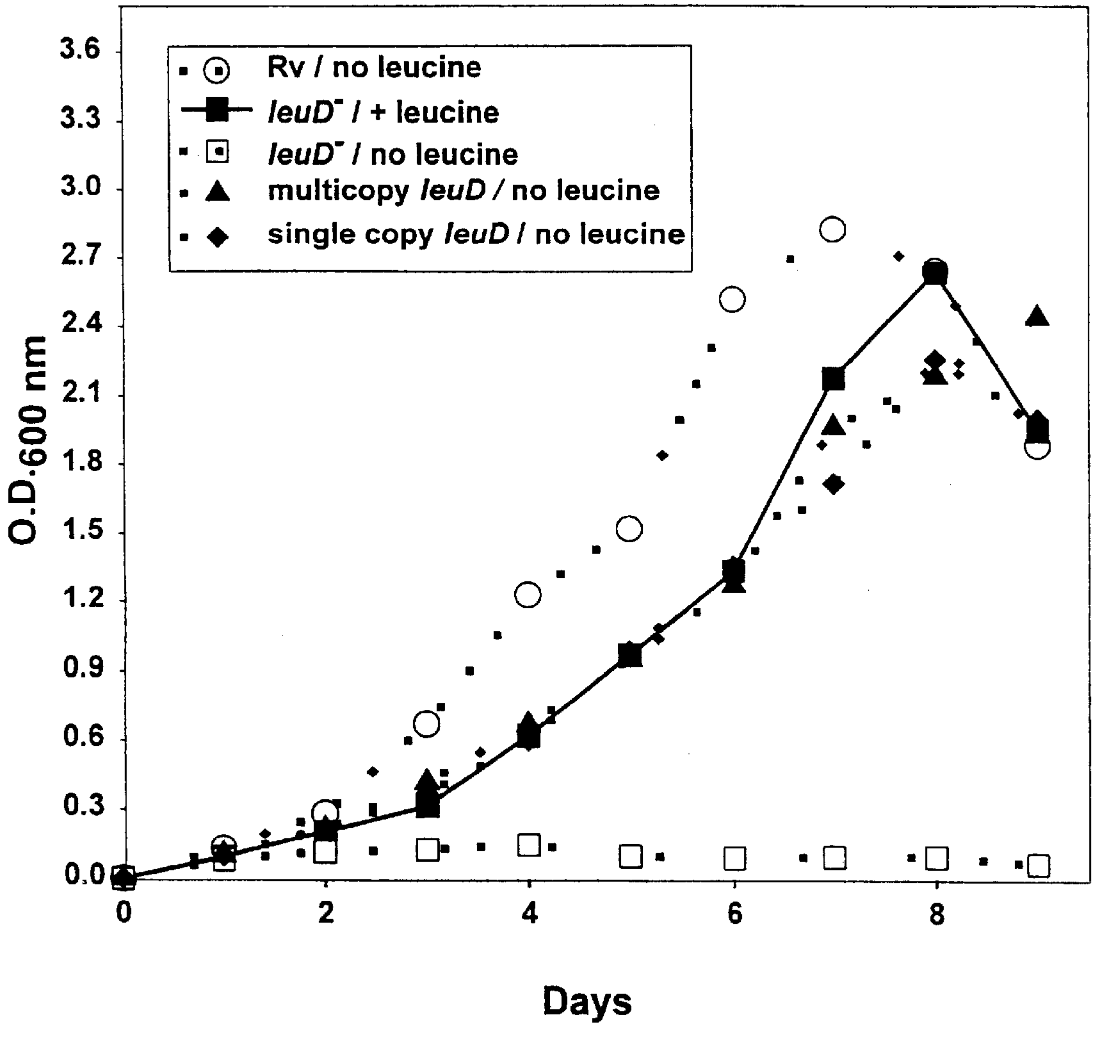

Until recently, creating defined mutants of slow-growing mycobacteria (MTB and BCG) has been difficult to achieve. However, thanks to recent advances, including the use of counter-selection, it was possible for us to generate a deletion mutant of MTB that required leucine for growth. To create this mutant, *M. tuberculosis* H37Rv was transformed with pMH10.1 a replicating vector that contained a mutant copy of leuD with a 359 bp deletion marked by a hygromycin cassette. There was 2230 bp of mycobacterial DNA 5' and 739 bp of sequence 3' to the hygromycin casette. In addition, this vector contained an aph gene encoding kanamycin resistance and sacB, the presence of which confers sensitivity to sucrose. Hygromycin resistant transformants were obtained and were confirmed to be both kanamycin resistant and sensitive to growth on plates with 3% sucrose. Ten individual cultures of 10 individual $hgm^r/km^r/suc^s$ clones were established and grown in complete media supplemented with leucine and hygromycin, as described above. Following plating on complete agar supplemented with leucine, hygromycin and sucrose, 334 $hgm^r/suc^r$ colonies, arising from the original 10 $hgm^r/km^r/suc^s$ clones, were picked into individual wells of 96-well plates containing media with hygromycin and leucine. The wells were subsequently frogged onto leucine supplemented plates containing either kanamycin or hygromycin or they were frogged onto mimimal plates without leucine supplementation. Greater than 90% of the frogged clones were $hgm^r/km^s$. However, 11 of 334 cultures were found to be $hgm^r/km^s/leu^-$. These 11 clones were derived from 4 of the original 10 $hgm^r/km^r/suc^s$ clones. Southern blot analysis confirmed that these 11 clones had indeed undergone an allelic replacement event, an example of one such $hgm^r$ $leu^-$clone, strain $mc^22032$, is provided in FIG. 1A. Wildtype genomic H37Rv DNA (lane 1) digested with Acc65I and probed with a 600 bp fragment of leuD yields a fragment of 2425 bp. In contrast, $mc^22032$ (lane 2) which has 359 bp deletion marked by a 1899 bp hygromycin cassette shows a band of 3965 bp and loss of the wildtype band, thus confirming the allelic exchange event. Strain $mc^22032$ failed to grow on minimal agar (FIG. 2A) or in minimal broth (FIG. 2C) however, growth could be restored with leucine supplementation (FIGS. 2B, 2C). The growth rate of $mc^23032$ in broth media supplemented with leucine was similar to that of wildtype H37Rv in leucine free media (FIG. 2C). However, the density of $mc^23032$ cultures were always slightly less than that of wildtype. As expected, complementation of $mc^22032$ with leuD provided in trans on a multicopy plasmid (strain $mc^23034$) or in single copy integrated at the att site ($mc^23035$) abolished the requirement for exogenous leucine (FIGS. 2B, 2C). To test the stability the phenotype, reversion or supressor mutant analysis of $mc^23032$ was performed two separate occasions. The strain was grown in leucine supplemented media without hygromycin and then plated on minimal agar. No leu+clones (out of $4–6\times10^{10}$ CFU plated) arose in either experiment. Thus, the reversion frequency was calculated at $<2\times10^{-11}$.

The Intracellular Growth Potential of $mc^23032$ is Impaired

Figure 3A:
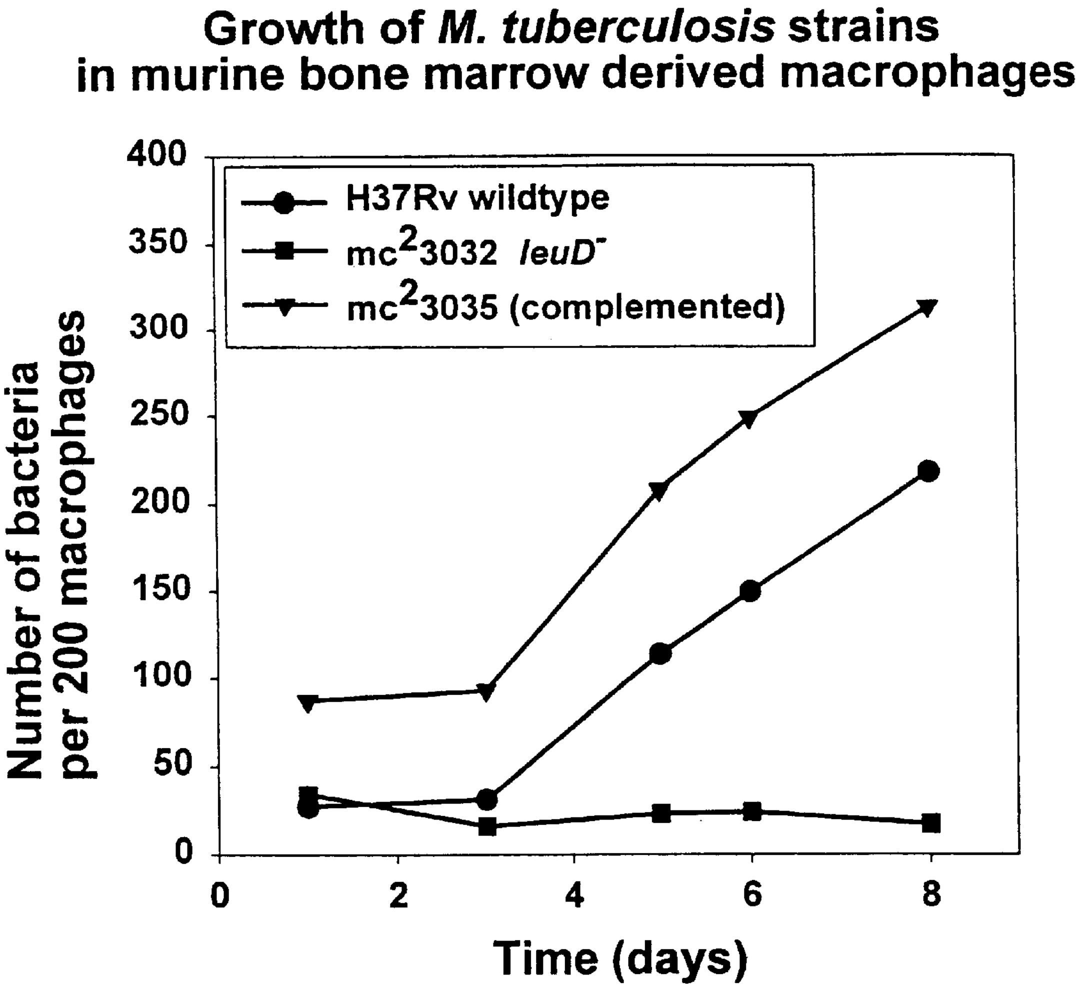
FIGS. 3A and 3B. Growth of *M. tuberculosis* H37Rv and a *M. tuberculosis* leucine auxotroph in murine bone marrow-derived macrophages in vitro. Bone marrow-derived macrophages were infected with wildtype H37RV (circles), strain $mc^2$3032 $leuD^-$ (squares) or strain $mc^2$3035 leuD+ complemented (diamonds) at an MOI of 2–20:1 bacteria per macrophage, as described in *Materials and Methods.* At various times post infection, macrophage monolayers were fixed and stained and examined under fluorescent microscopy. A) The number of bacteria associated with 200 macrophages was enumerated by visual inspection of the monolayers. Heavily burdened macrophages were scored as containing of 10 bacteria. B) The number of bacteria per infected macrophage (out of 200 counted) over time post infection. Data is expressed as the mean of duplicate samples. The figure is representative of 3 independent experiments.
Figure 3B:
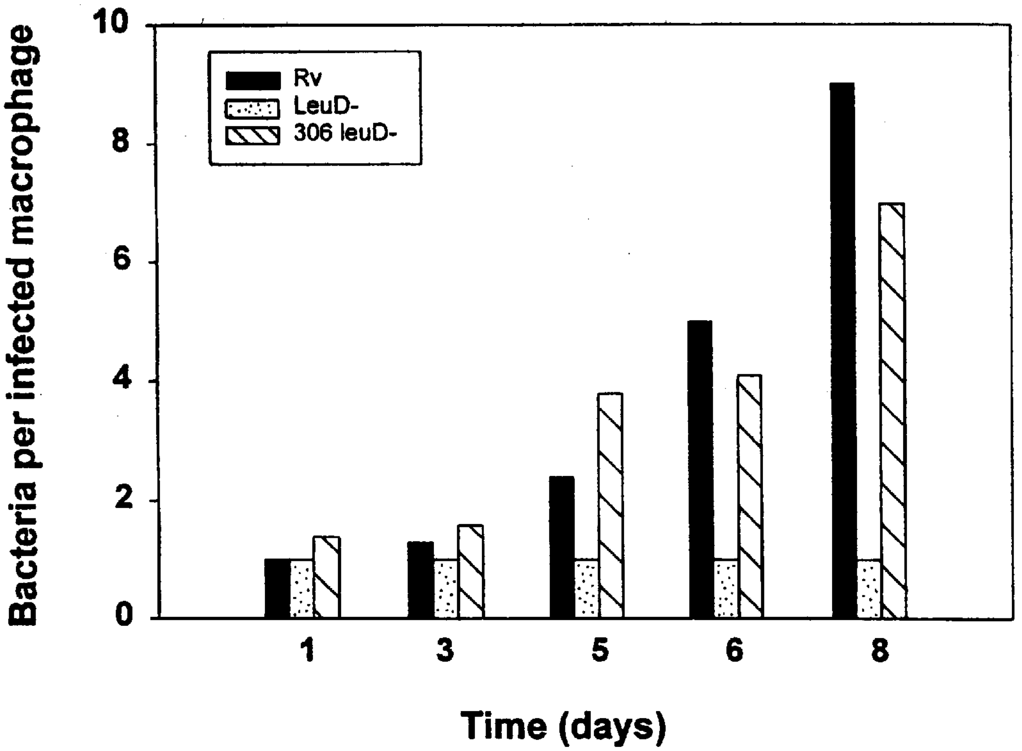

In order to determine if the requirement for exogenous leucine supplementation could affect the ability of the leuD mutant to undergo intracellular replication, we examined the behavior of the leucine auxotroph in cultured macrophages in vitro. Bone marrow-derived macrophages from BALB/cJ mice were infected with either wildtype H37Rv, $leuD^-$ $mc^23032$ or $mc^23035$, the leuD complemented strain. Following adsorption at a MOI of 2–10 bacteria per macrophage, unbound bacteria were removed by extensive washing of the monolayer, and gentomicin was added to kill extracellular bacteria. The MOI used resulted in approximately 15–30% infection of the monolayer, with each infected macrophage containing approximately 1–2 bacteria per cell. At various times post infection, monolayers were fixed with formalin, stained, and the number of bacteria associated with 200 macrophages was enumerated by counting under fluorescence microscopy. Following a 72 h lag period, the numbers of both wildtype H37Rv and the complemented strain $mc^23035$ associated with the macrophage monolayer began to increase such that at 8 days post infection, the intracellular bacilli had expanded by approximately 10 and 7-fold respectively (FIG. 3A). The growth of these strains was also reflected as an increase in the number of bacteria per infected macrophage (FIG. 3B). At later timepoints, it was difficult to accurately count large bacterial numbers, so that macrophages containing 10 or greater bacteria were simply scored as containing 10 bacilli. Thus, bacterial replication was undoubtedly greater than that reflected. Throughout the course of the experiment, the percentage of the monolayer that was infected remained virtually unchanged, indicating that macrophage lysis and subsequent reinfection was minimal (data not shown). In contast to the wildtype strain and the leuD complemented mutant, strain $mc^2$3032, the leucine auxotroph, failed to replicate inside of macrophages, and its numbers began to decrease with time post infection. Thus, the inability of the strain $mc^2$3032 to make leucine rendered it incapable of intracellular growth.

$mc^2$3032 $LeuD^-$ is Attenuated in SCID Mice

Figure 4:
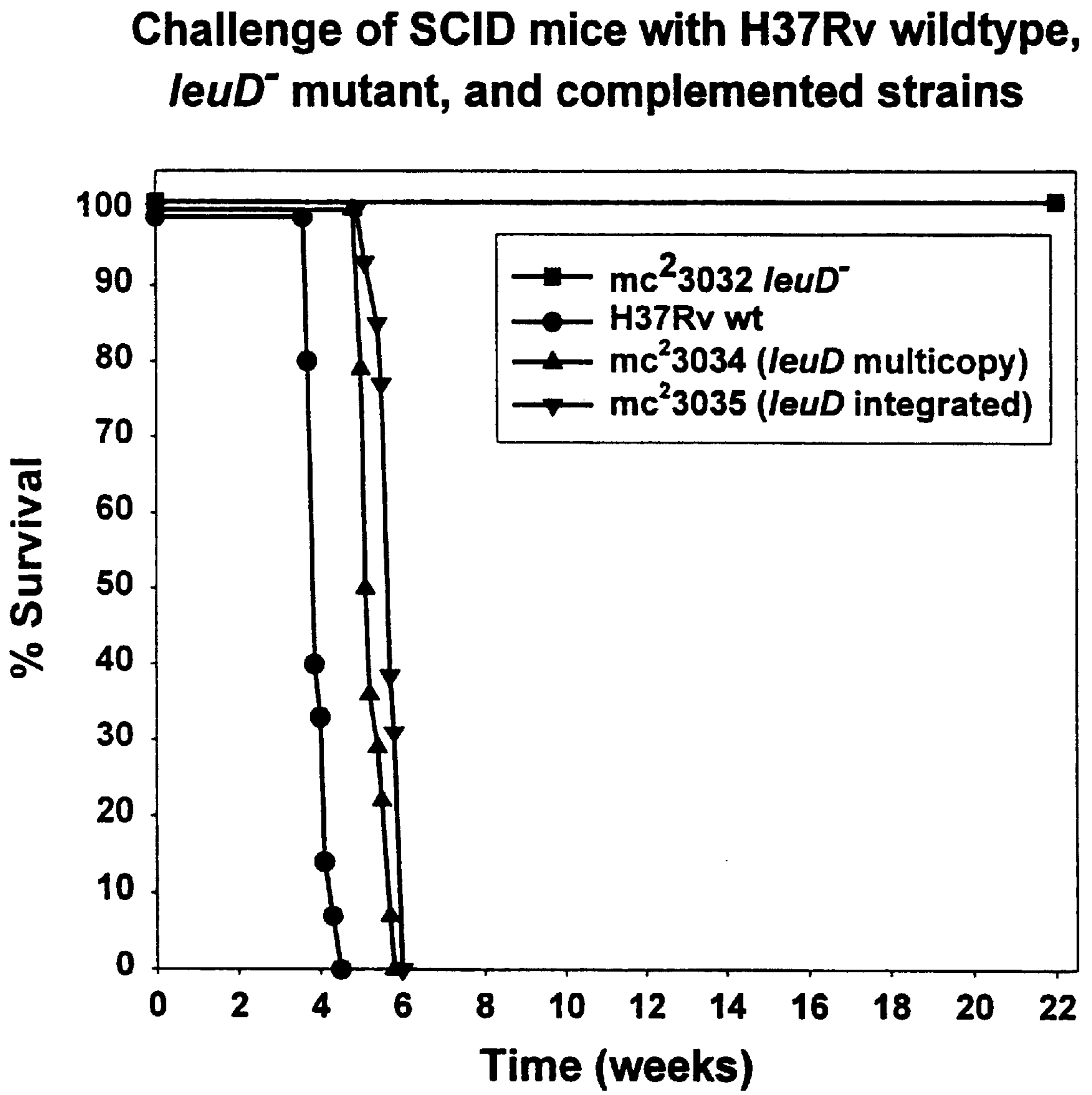
FIG. 4. Survival of SCID mice infected with various strains of *M. tuberculosis.* BALB/cJ SCID mice were challenged by the intravenous route with $1\times10^4$ CFU of H37Rv wildtype (circles), or $1\times10^6$ CFU of $mc^2$3032 $leuD^-$ (squares), or with $1\times10^4$ CFU of the leud complemented strains $mc^2$3034 (triangles) (leuD in multicopy on a plasmid) or $mc^2$3035 (diamonds) (leuD in single copy integrated on the chromosome). Each experimental group consisted of 13–14 mice. This experiment was performed twice with similar results.

Based on the in vitro data showing that the leucine auxotroph ($mc^2$3032 ) cannot replicate within macrophages, it follows that strain $mc^2$3032 would be attenuated for growth in vivo. To test the effect of leucine auxotrophy on MTB virulence, SCID mice, lacking B and T cells, were infected with wildtype H37Rv, $mc^2$3032 $leuD^-$, or the complemented strains $mc^2$3034 or $mc^2$3035. SCID mice are exquisitely susceptible to MTB infection and will succumb to an intravenous challenge of $1\times10^4$ CFU of wildtype H37Rv in a month's time (FIG. 4). Bacterial burdens in these animals reached $5.8\times10^8\pm3.6\times10^8$ CFU in the livers, $6.4\times10^7\pm3.2\times10^7$ CFU in the spleens, and $3.8\times10^7+4\times10^7$ CFU in lungs at the time of death. In contrast, SCID mice receiving strain $mc^2$3032 at approximately a 100-fold greater inoculum were able to clear the infection and remained healthy for 22 weeks, at which time the experiment was terminated (FIG. 4). No bacilli could be cultured from the lungs or spleens of these animals, but a few (14 total) colonies were recovered from the livers of 5 mice. These colonies failed to grow without leucine supplementation, and were therefore not suppressor mutants.

Infection of SCID mice with the leuD complemented strains $mc^2$ 3034 and $mc^2$3035, at an inoculum equal to that of wildtype H37Rv, was lethal, and the animals died with virtually identical kinetics which were similar but slightly delayed to that of wildtype (FIG. 4). Bacterial burdens in the organs at the time of death were comparable to that found in animals dying as a result of infection with wildtype bacilli. Restoration of virulence with wildtype leuD provided in either multicopy or in single copy established that the observed attenuation of strain $mc^2$3032 was attributable to the mutation in leuD that conferred leucine auxotrophy and was not due to a downstream polar effect.

Figure 5:
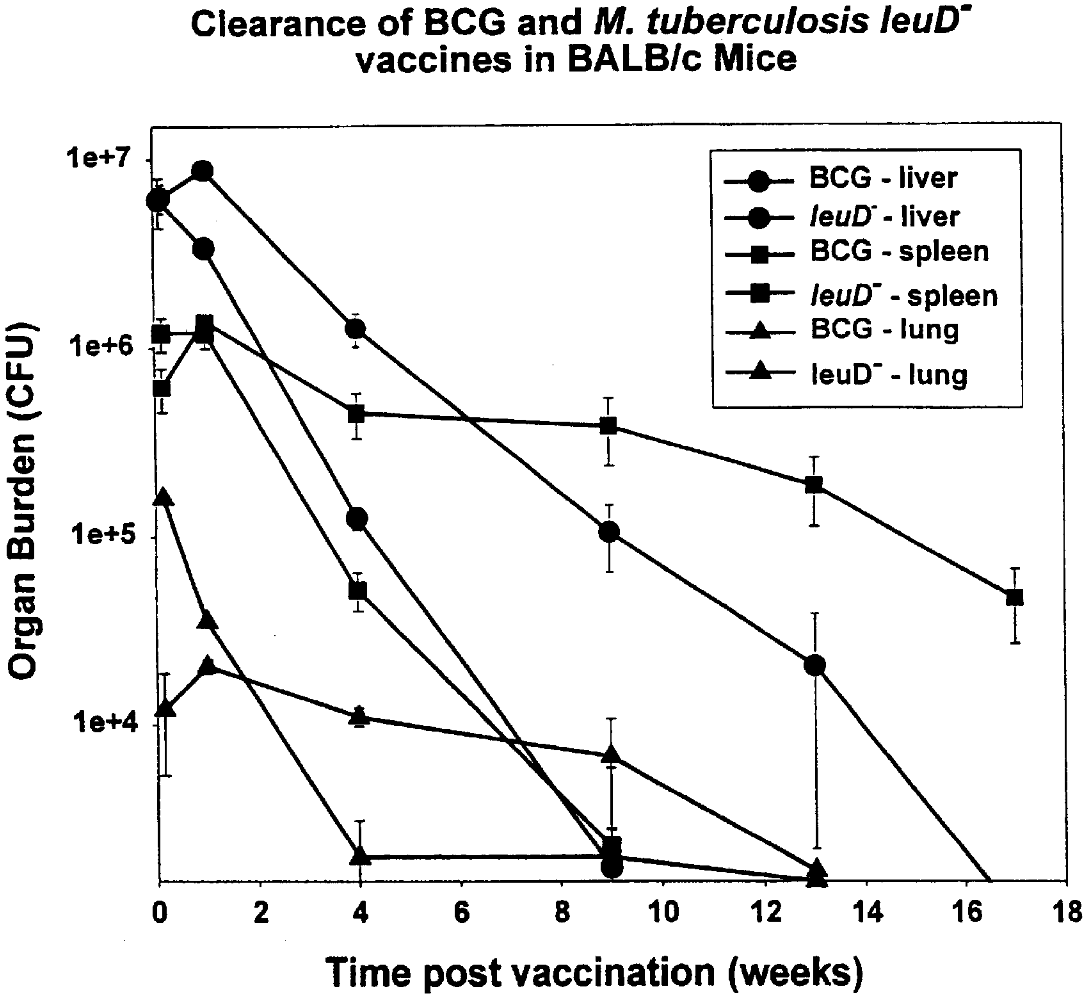
FIG. 5. Clearance of *M. bovis* BCG and $mc^2$3032 in the tissues of immunocompetent BALB/cJ mice. Mice were immunized via the lateral tail vein with $5\times10^6$ CFU of *M. bovis* BCG (open symbols) or a similar number of $mc^2$3032 $leuD^-$ (closed symbols). At the indicated times after immunization, mice were sacrificed and their organs collected and homogenized. The bacterial burden in the lungs, spleen, and liver were determined by serial dilution and plating of the homogenate onto leucine supplemented media. The error bars represent the standard deviation for the mean of 4–5 mice per experimental group.

Persistance and Protective Efficacy of Strain $mc^2$3032 and Comparisons with BCG Having established that the leucine auxotroph of *M. tuberculosis* was indeed attenuated in immunocompromised animals, a requirement of any new tuberculosis vaccine, we next sought to determine whether it could elicit protective immunity against a challenge with virulent organisms. Immunocompetent BALB/cJ mice, a-strain relatively susceptible to *M. tuberculosis,* were intravenously immunized with $5\times10^6$ CFU of $leuD^-$ $mc^2$3032. Similarly, a group of animals were immunized with the conventional tuberculosis vaccine, BCG strain Pasteur. Following immunization, the bacterial burden in the spleens and livers of $mc^2$3032 immunized animals remained steady for a week, whereas bacterial numbers in the lung had decreased by 10-fold (FIG. 5). Thereafter, a steady decline ensued, such that by 13 weeks, the leucine auxotroph could not be recovered from any tissues examined (FIG. 5). In contrast, immunization with BCG was followed by a slight increase in bacterial numbers in the spleen and liver. Clearance of BCG in all tissues was delayed, as compared to that of $mc^2$3032 immunized animals. In fact, at 16 weeks post immunization, the splenic BCG burden had declined by only 1 log (FIG. 5).

Figure 6A:
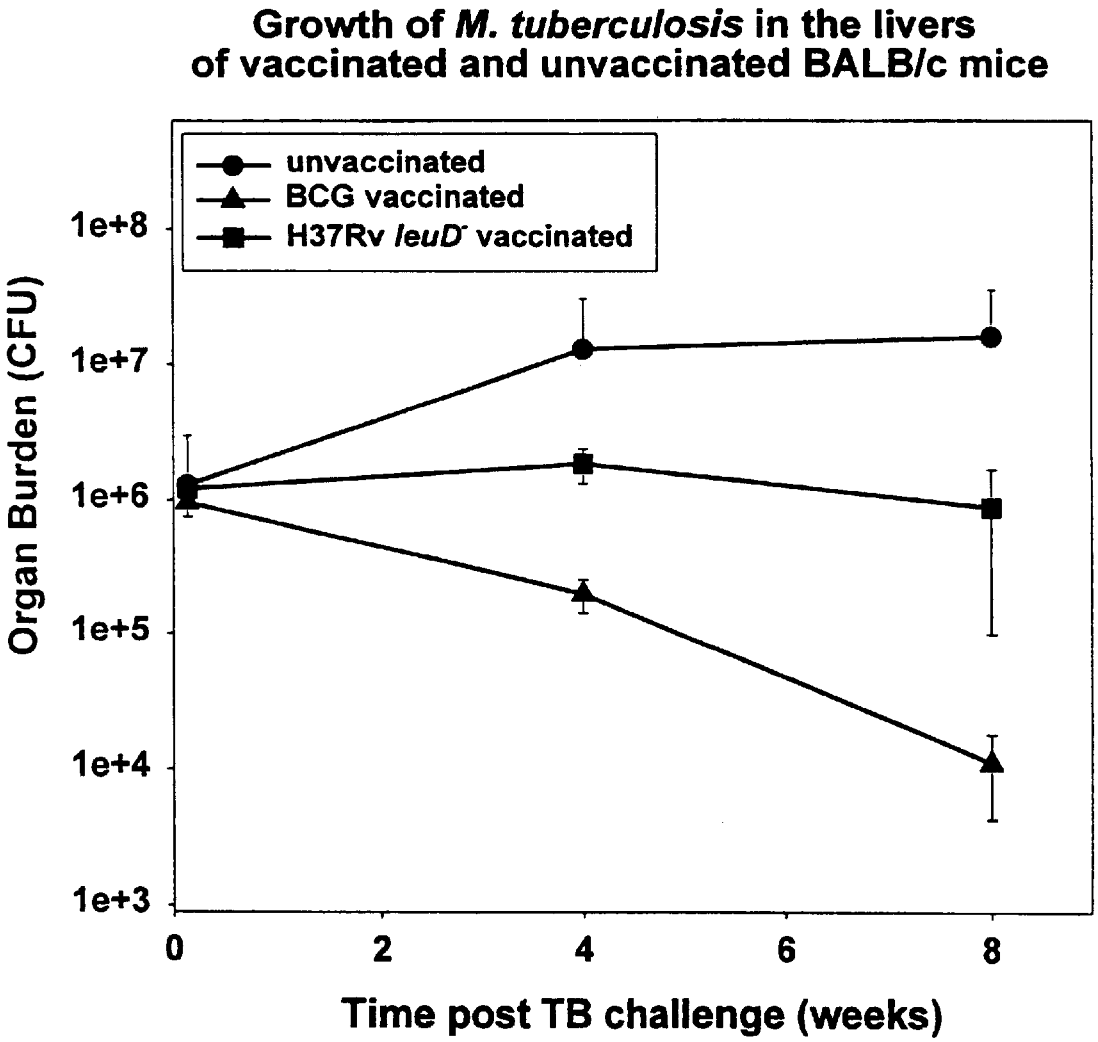
FIGS. 6A–6C. Growth of virulent *M. tuberculosis* in the tissues of vaccinated and unvaccinated mice. BALB/Cj mice were challenged intravenously with $1\times10^6$ CFU of virulent *M. tuberculosis* 9 weeks post intravenous vaccination with either *M. bovis* BCG or $mc^2$3032 $leuD^-$. At various times following immunization, mice were sacrificed and their organs collected and homogenized. The bacterial burden in the liver (6A), spleen (6B) and lungs (6C) were determined by serial dilution and plating of the homogenate. The error bars represent the standard deviation for the mean of 4–5 mice per experimental group.
Figure 6B:
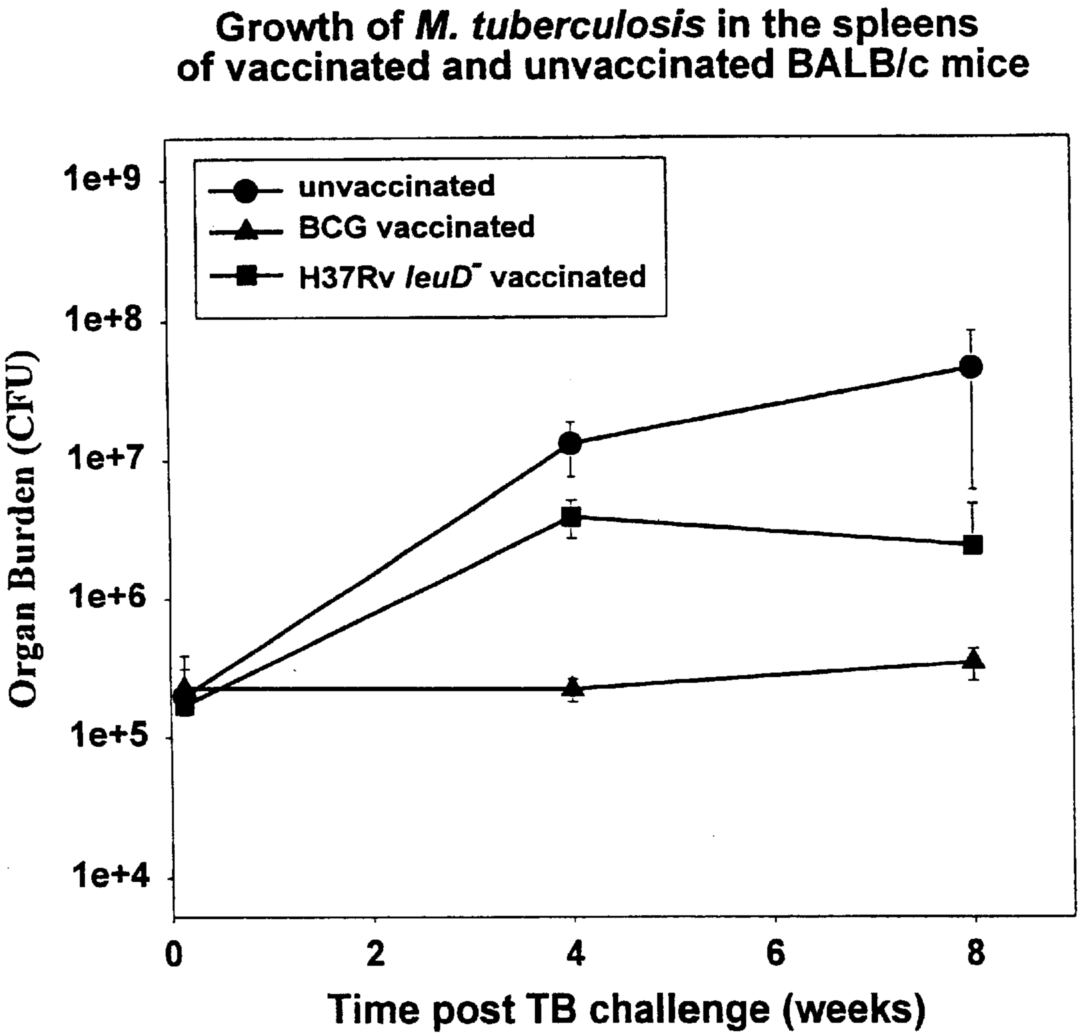
Figure 6C:
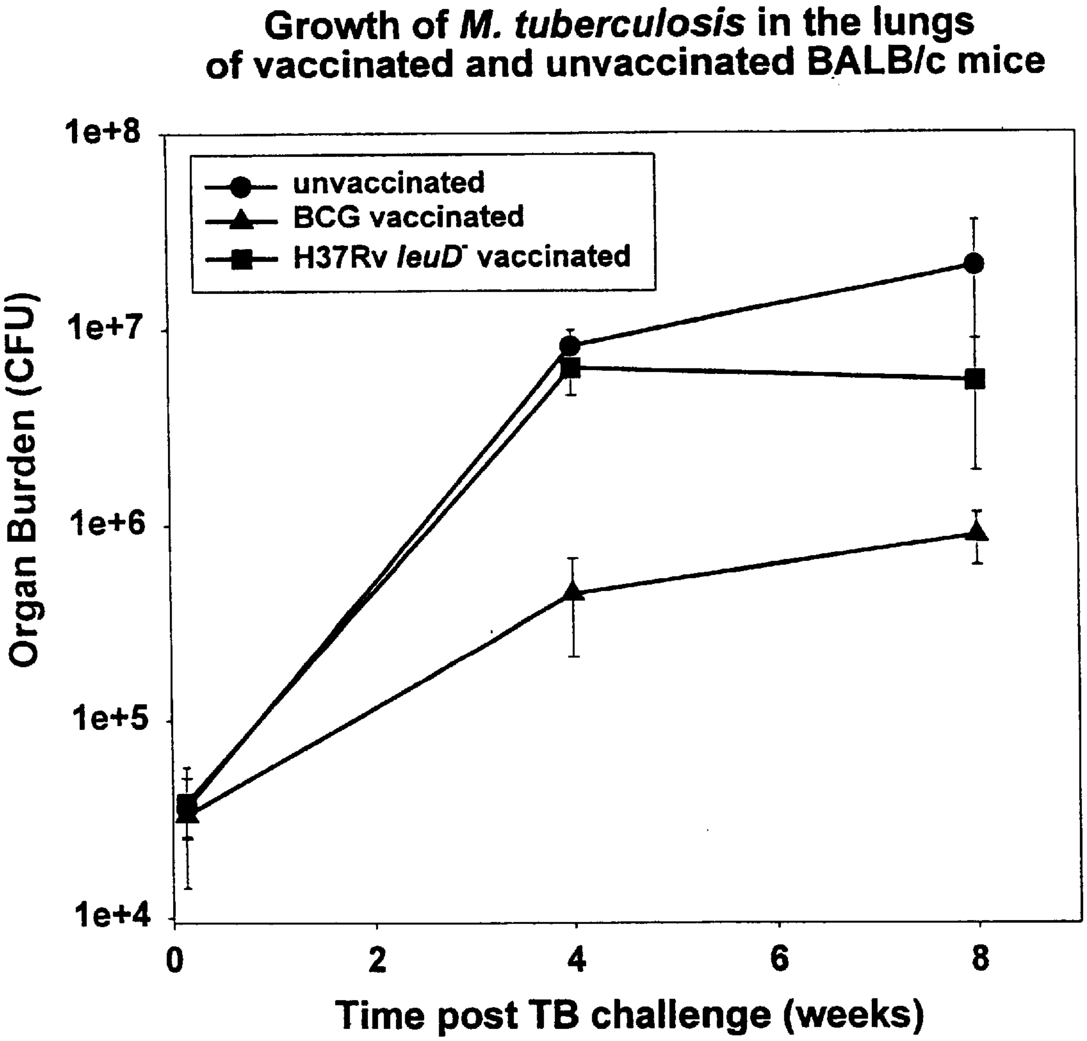
Figure 7:
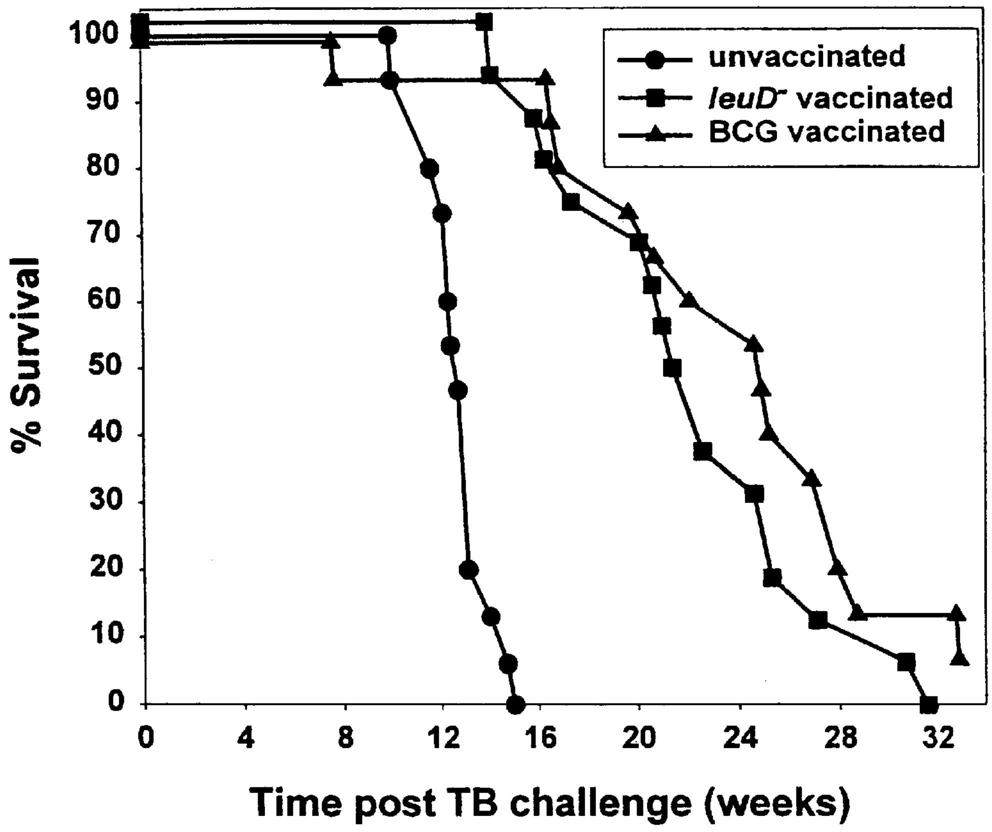
FIG. 7. Survival of vaccinated and unvaccinated mice subsequent to a challenge with virulent *M. tuberculosis.* Immunocompetent BALB/cJ mice were given $1\times10^6$ CFU of virulent *M. tuberculosis* by intravenous injection. The survival of these animals was followed and is expressed as percentage of the experimental group surviving over time. Each group consisted of 15–16 mice.

To test the protective efficacy of the vaccines, 9 weeks post immunization, the vaccinated animals and unimmunized controls were challenged intravenously with $1\times10^6$ CFU of virulent *M. tuberculosis.* Bacterial burdens in unimmunized animals steadily rose in all tissues, increasing by approximately 1 log in the liver, 2 logs in the spleen, and 2.5 logs in the lung at 8 weeks post challenge (FIGS. 6A, 6B, and 6C). By 15 weeks post infection, all unvaccinated animals had succumbed to disease (FIG. 7). Mean bacterial burdens at the time death had reached $3.8\times10^8\pm2.3\times10^8$ CFU in the spleen, $7.88\times10^7$ CFU$\pm6.5\times10^7$ CFU in the liver, and $7.6\times10^8+7\times10^8$ CFU in the lung. In contrast, consistent with published results, BCG vaccination slowed the growth of wildtype *M. tuberculosis* in all tissues examined (FIGS. 6A, 6B, and 6C) and prolonged the survival of the mice by several weeks (FIG. 7). Likewise, mice previously immunized with $leuD^-mc^2$3032 also exhibited enhanced survival that was statistically equivalent (p=0.001) to the BCG vaccinated group (FIG. 7).

Despite the comparable efficacy of BCG and $mc^2$3032 in enhancing survival against a lethal challenge of virulent *M. tuberculosis,* differences between the two vaccinated groups were apparent. Specifically, at 2 months post challenge, bacterial numbers in the lungs of BCG vaccinated mice were approximately 1.5 logs lower relative to unvaccinated controls, and bacterial expansion was halted in the spleen while clearance was occurring in the liver. In contrast to BCG vaccinated animals, mice vaccinated with $leuD^-$ $mc^2$3032 displayed a reduced level of protection; bacterial burdens were higher with this group in all organs.

C. Discussion

The creation of a leucine auxotroph of *M. tuberculosis,* in which the wildtype gene leuD was replaced with a mutated copy by allelic exchange, is described above. Until very recently, it has been difficult to create defined mutants of *M. tuberculosis*, a factor that has hampered the genetic analysis of this important pathogen. Although allelic replacement was successfully performed by several groups in the rapidly-growing, non-pathogenic, *M. smegmatis,* (Husson, et al., *J. Bacteriol.,* 172:519–524 (1990); Kalpana, et al., *PNAS USA,* 88:5433–5437 (1991); Sander, et al., *Mol. Microbiol.,* 16:991–1000 (1995), Pavelka, et al., *J. Bacteriol.,* 178:6496–6507 (1996)), the slow-growing *M. tuberculosis* complex members including *M. tuberculosis, M. bovis* and *M. bovis* BCG proved to be less amenable to such genetic manipulations. Early attempts at gene exchange using a nonreplicating, suicide vector approach were unsuccessful and yielded either single-crossover transformants (Aldovoni, et al., *J. Bacteriol.,* 175:7282–7289 (1993)) or resulted in a high incidence of non-homologous, illegitimate recombination (Kalpana, et al., *PNAS USA,* 88:5433–5437 (1991); Aldovonia, et al., 1993). Reasons given to explain the initial lack of success included low levels of transformation efficiency, a high background of random non-homologous integration, and the effects of an intein within the open reading frame of the recombination-influencing recA gene (McFadden, *Mol. Micro.,* 21:205–211 (1996)). However, in the last 3 years, several groups have achieved allelic replacement in the previously genetically refractive slow-growing species (Reyret, et al., *PNAS USA,* 92:8768–8772 (1995); Balasubramanian, et al., *J. Bacteriol.,* 178:273–279 (1996); Azad, et al., *PNAS USA,* 93:4787–4792 (1996)). These earliest successes were laboriously achieved and accomplished by screening numerous erroneous clones. However, the subsequent use of the counter-selectable marker, sacB, a gene from *B. subtilis* conferring sucrose sensitivity, reduced the number of clones that had to be screened in order to identify an allelic exchange mutant (Azad, et al., *J. Biol. Chem.,* 272:16741–16745 (1997); Pelicic, et al., *PNAS USA,* 94:10955–10960 (1997)). Coupling this counter-selection with a temperature sensitive origin of replication, further enhanced the identification of double homologous recombinants, but the necessity for growth at the lower permissive temperature (32° C.) greatly prolonged the time required to generate the desired mutant (Giguel, personal comm.).

In creating a leuD mutant of *M. tuberculosis,* the present invention also employed the use of sacB. This counter-selectable marker was simply cloned into a standard episomal Mycobacterium-*E. coli* shuttle vector, (pMv261) (Stover, et al., *Nature,* 351:456–460 (1991)) creating pMP7, and despite the absence of a conditional replicon, we were able to obtain the desired double homologous deletion mutant. Nevertheless, the approach was somewhat less than optimal, since only 11 or 3% of the 334 hygromycin-resistant, sucrose resistant clones screened by replica plating, were the desired leucine auxotrophs. In the vast majority of these sucrose resistant, leu+clones, a deletion had occurred in the plasmid backbone, such that both the kanamycin resistant marker and sacB were lost (data not shown). This finding prompted us to reconstruct the replicating vector, such that sacB and aph were separated by the marked-mutant gene of interest on one side of the plasmid and the origin of replication (oriM) on the other. Thus, with antibiotic selection for the mutant allele (hygromycin), deletion of both sacB and aph would have to occur as two independent events. The modification greatly improved the success of this replicating vector approach to allelic exchange. When it was used to create a different mutant, 77% of the $hgm^r/km^s$ clones were determined to have undergone the correct allelic exchange event (data not shown, M. Glickman, personal communication). Thus, this replicating, sacB-containing vector will facilitate both the production and identification of double homologous recombinants, and it should prove useful in strains of mycobacteria in which transformation efficiency is too low to achieve either a double-or single-crossover recombination event using a non-replicating suicide vector.

Through the creation of a leucine auxotroph of *M. tuberculosis,* we hoped to learn something about the nature of the intracellular environment in which this organism resides. The availability of nutrients is crucial to the survival of any microbe and is particularly essential to those living in an intracellular location. Organisms must evolve mechanisms to access nutrients or face eventual elimination. For instance, virulent *Listeria monocytogenes,* a facultative intracellular pathogen naturally auxotrophic for 7 amino acids (arginine, cysteine, Gln, isoleucine, leucine, methionine, and valine) expresses a hemolysin that facilitates bacterial escape from the phagosome into the amino acid rich cytosol, wherein the bacterium readily replicates (Marquis, et al., *Infect. Immun.* 61:3756–3760 (1993)). Pathogens whose intracellular lifestyle is confined to the phagosome may modify their vacuolar environment to allow acquisition of nutrients. For example, the parasites *Toxoplama gondii* and *Plasmodium falciparum* both establish pores within the parasitophorous vacuole through which small cytosolic molecules can diffuse (Schwab, et al., *Mol. Biol. Cell.,* 3(Suppl.):303a (1992); Desai, et al., *Nature,* 362:643–646 (1993)). The intracellular bacterium, *Legionella pneumophia,* has very complex growth requirements, yet it is able to replicate within macrophage vacuoles. Vacuoles containing wildtype legionella fail to fuse with lysosomes and become surrounded by both mitochondria and rough endoplasmic reticulum, whereas certain mutant strains do not, (Berger, et al., *Mole. Microbiol.,* 14:797–808 (1994)) implying that the bacterium may actively modify the vacuolar compartment (Horwitz, *J. Clin. Invest.,* 66:441–450 (1983); Swanson and Isberg, *Infect. Immun.,* 63:3609–3620 (1995)). Likewise, mycobacteria spp. can influence macrophage endosomal trafficing; the proton-ATPase responsible for acidification of the phagosome is excluded, and a particular host protein (termed TACO for tryptophan aspartate-containing coat protein) is actively retained on the phagosomal membranes enclosing viable bacilli (Sturgill-Koszycki, et al., *Lancet,* 347:358–362 (1994)). Thus mycobacterium spp. evolved means to modify their intracellular environment, and perhaps some modifications allow for the exploitation of host nutrients.

The connection between bacterial metabolism and virulence was established almost fifty years ago when Bacon and colleagues mutagenized a virulent strain of *Bacterium typhosum* (*Salmonella typhi*) and showed that certain mutants, including those requiring leucine, purines, or para-amino benzoic acid for growth, were less virulent for mice (Bacon, et al., *Brit. J. Exp. Path.,* 31:714–723 (1950)). They attributed this loss of virulence to restricted host tissue availability of the required growth factor. An important feature of their work was the finding that the vast majority of the auxotrophic mutants they generated were fully virulent (Bacon, et al., 1950). Thus, without knowing the specifics of an organism's lifestyle, there is no reason a priori to assume that auxotrophy will affect virulence. Nevertheless, since these early studies, several groups have reported auxotrophic mutants of *Salmonella typhimurium, Legionella pneumophlia, Shigella flexneri,* and *Corynebacterium pseudotuberculosis* to be attenuated for growth either in vitro within macrophages or in animals in vivo (Hoiseth and Stocker, *Nature,* 291:238–239 (1981); Fields, et al., *PNAS,* 83:5189–5193 (1986); Leung and Finlay, *PNAS,* 88:11470–11474 (1991); Mintz, et al., *Infect. Immun.,* 56:1449–1455 (1988); Ahmed, et al., *Vaccine,* 8:153–158 (1990); Okada, et al., *Mol. Microbiol.,* 5:187–195 (1991); Simmons, et al., *JAMA,* 68:764 (1997)). Likewise, several auxotrophs of *M. bovis* BCG, including two with insertions in leuD, have been shown to be attenuated in mice (McAdam, et al, *J. Clin. Invest.,* 66:441–450 (1995); Guleria, et al., *Nature Med.,* 2:334–337 (1996)). The attenuation of the leucine auxotroph was later correlated with an inability of this strain to replicate in macrophages in vitro (Bange, et al., *Infect. Immun.,* 66:2951–2959 (1996)), providing an explanation for the attenuated phenotype. These observations prompted us to ask whether a $leuD^-$ auxotroph of *M. tuberculosis* would exhibit the same growth restrictions. The present invention answers that question by demonstrating that *M. tuberculosis* with a deletion mutation in leuD, is indeed incapable of replication either in macrophages (FIG. 3) or in mice (FIGS. 4 and 5). The attenuated phenotype is due to the mutation in leuD since both intracellular growth and virulence can be restored by complementation with a wildtype copy of the gene. Thus the intracellular environment of *M. tuberculosis* must be such that the availability of leucine is limiting.

Once we established that strain $mc^23032$ $leuD^-$ was attenuated, we questioned whether it could be useful as a vaccine, as has been described for auxotrophs of other bacterial species. The prototype auxotroph vaccine was created by Hoiseth and Stocker (*Nature,* 291:238–239 (1981)), who used Tn10 mutagenesis to generate an aroA mutant of *S. typhimurium,* a strain requiring exogenous aromatic amino acids, para-amino-benzoic acid, and dihydrobenzoic acid for growth. As these compounds are not products of mammalian metabolism, and are in short supply in vivo, the mutant was rendered severely compromised and virtually incapable of inducing a fatal infection of mice. However, the aroA strain could immunize and prevent death of animals challenged with a lethal dose of virulent *S. typhimurium.* (Hoiseth and Stocker, 1981). Subsequent to this early work, auxotrophic mutants of several bacterial pathogens including *Salmonella typhi, Salmonella dublin, Salmonella enteritidis, Yersinia pestis, Shigella flexneri,* and Corynebacterium spp., have been shown to be attenuated in vivo yet capable priming an immune response in several animal species and humans (Dougan, et al., *Mol. Gen. Genet.,* 207:402–405 (1987); Bowe, et al., *Infect. Immun.,* 57:3234–3236 (1989); Simmons et al., *Infect. Immun.,* 65:3048–3056 (1997)). Recently, it was shown that leucine, isoleucine-valine, and methionine auxotrophs of *M. bovis* BCG, although attenuated for growth in vivo, are still effective in providing protection against a challenge of virulent *M. tuberculosis* (Gulieria, et al., *Nature Med.,* 2:334–337 (1996)). Likewise, in this work we have demonstrated that an attenuated leucine auxotroph of *M. tuberculosis* ($mc^2$3032) can induce protective immunity to a virulent strain of the same organism. Protection was manifest by both a reduction in tissue pathology and enhanced survival post-challenge, survival that was statistically equivalent to that of animals immunized with the conventional BCG vaccine.

Any experimentation with regard to protection against *M. tuberculosis* generally includes comparisons to the currently and widely used *M. bovis* BCG vaccine. This comparison is reasonable, as BCG has frequently faltered in safeguarding vaccinates against tuberculosis, spurring the compulsion to create a better vaccine. Despite its shortcomings, substantial evidence, both experimental (Opie, et al., *J. Exp. Med.,* 66:761–788 (1937); Hubbard, et al., *Clin. Exp. Immunol.,* 87:94–98 (1992); Baldwin, et al., *Infect. Immun.,* 66:2951–2959 (1998)) and clinical (MRC and Eskimo trials) exists to support the notion that BCG vaccination engenders immunity to *M. tuberculosis.* Likewise, it is well established that live bacilli induce more effective immunity than killed bacilli (Opie, et al., *J. Exp. Med.,* 66:761–788 (1937); Smith, *JAMA,* 68:764 (1917); Zinsser, et al., *J. Immunol.,* 10:719 (1925)), and that optimal protection is associated with replication of the bacillus in host tissues (Dubos and Schaefer, *Am. Rev. Tuberculous Pulmonary Dis.,* 74:541–551 (1956)). Treatment with antimicrobials that hinder the expansion of the organism in vivo will oppose the development of protective immunity (Dubos and Schaefer, 1956). However, the effect of chemoprophylaxis can be overcome if the vaccinated dose is large (Dubos and Schaefer, 1956). Bacterial replication in vivo likely influences both the quantity and quality of antigen available to the immune system. Thus, a limitation of killed vaccines is that certain antigens will not be represented, as they are expressed only in vivo (Mckenney, et al., *Science,* 284:1523–1527 (1999)).

The above findings are relevant to the discussion of the leucine auxotroph of *M. tuberculosis* that we have created and examined herein. The $leuD^-$ *M. tuberculosis* is attenuated, even in immunocompromised hosts, a trait desirable in a live vaccine, particularly one in which many of the vaccine recipients will be at risk for developing AIDS. Moreover, the leucine auxotroph was as good as BCG in prolonging the survival of mice challenged with virulent *M. tuberculosis.* In addition, the lungs of mice immunized with the leucine auxotroph displayed less pathology than that of control unimmunized animals. However, immunization with BCG better restricted the growth of virulent bacilli in all tissues examined, and was associated with even less pathology. Although the $leuD^-$ mutant could induce a protective immune response, it was somewhat compromised in doing so, likely because of the inaccessiblity of leucine limits the ability of the strain to express relevant antigens in vivo. Such a limitation might be expected to afflict many types of auxotrophs of *M. tuberculosis.* Recently, it has been shown that purine auxotrophs of BCG and *M. tuberculosis,* are attenuated for growth in macrophages and survival in vivo (Jackson, et al., *Infect. Immun.,* 67:2867–2873 (1999)). Furthermore, guinea pigs vaccinated with these strains were able to restrict the growth of virulent *M. tuberculosis* in their lungs. However, both of these purine mutants were less able than conventional BCG to limit the growth of *M. tuberculosis* in the spleen, in fact, the BCG purine auxotroph showed no protection in this organ (Jackson, et al., 1999). Mutations that severely cripple an organism may make it impotent as a vaccine. It is likely that for optimal immune priming, a vaccine strain will need to replicate briefly in vivo, to ensure that relevant antigens are expressed. Nevertheless, vaccination with a larger immunizing dose or booster immunizations may improve the immunogencity of attenuated strains.

While the foregoing invention has been described in some detail for purposes of clarity and understanding, it will be appreciated by one skilled in the art from a reading of the disclosure that various changes in form and detail can be made without departing from the true scope of the invention in the appended claims.

What is claimed is:

1. A method of treating tuberculosis in a subject, the method comprising administering to the subject a recombinant *M. tuberculosis* that is auxotrophic for leucine, in an amount effective to treat tuberculosis in the subject, wherein the *M. tuberculosis* either:

(a) comprises a deletion or point mutation of the leuD gene, (b) is auxotrophic for leucine as a result of a deletion mutation of the leuD gene generated by allelic exchange, or (c) is formulated with a carrier that renders the *M. tuberculosis* more immunogenic.

2. The method of claim 1, wherein the *M. tuberculosis* comprises a deletion or point mutation of the leuD gene.

3. The method of claim 1, wherein the *M. tuberculosis* is auxotrophic for leucine as a result of a deletion mutation of the leuD gene generated by allelic exchange.

4. The method of claim 1, wherein the *M. tuberculosis* is formulated with a carrier that renders the *M. tuberculosis* more immunogenic.

5. A method for inducing immunity to *M. tuberculosis* in a subject, the method comprising administering to the subject a recombinant *M. tuberculosis* that is auxotrophic for leucine, wherein the *M. tuberculosis* either comprises a deletion or point mutation of the leuD gene or is auxotrophic for leucine as a result of a deletion mutation of the leuD gene generated by allelic exchange.

6. The method of claim 5, wherein the *M. tuberculosis* comprises a deletion or point mutation of the leuD gene.

7. The method of claim 5, wherein the *M. tuberculosis* is auxotrophic for leucine as a result of a deletion mutation of the leuD gene generated by allelic exchange.

8. The method of claim 5, wherein the recombinant *M. tuberculosis* is formulated in a carrier that renders the recombinant *M. tuberculosis* more immunogenic.

9. The method of claim 5, wherein the recombinant *M. tuberculosis* is administered in conjunction with a suitable pharmaceutical carrier.

10. The method of claim 5, wherein the recombinant *M. tuberculosis* is administered to the subject by injection.

11. The method of claim 2, wherein the recombinant *M. tuberculosis* is formulated in a carrier that renders the recombinant *M. tuberculosis* more immunogenic.

12. The method of claim 2, wherein the recombinant *M. tuberculosis* is administered in conjunction with a suitable pharmaceutical carrier.

13. The method of claim 2, wherein the recombinant *M. tuberculosis* is administered to the subject by injection.

14. The method of claim 6, wherein the recombinant *M. tuberculosis* is formulated in a carrier that renders the recombinant *M. tuberculosis* more immunogenic.

15. The method of claim 6, wherein the recombinant *M. tuberculosis* is administered in conjunction with a suitable pharmaceutical carrier.

16. The method of claim 6, wherein the recombinant *M. tuberculosis* is administered to the subject by injection.

* * * * *